United States Patent
Kramer et al.

(10) Patent No.: US 9,603,588 B2
(45) Date of Patent: Mar. 28, 2017

(54) COMPRESSIBLE ARTERIOTOMY LOCATOR FOR VASCULAR CLOSURE DEVICES AND METHODS

(75) Inventors: Scott A. Kramer, Minneapolis, MN (US); Valerie J. Glazier, Eden Prairie, MN (US); Catherine A. Pipenhagen, Chanhassen, MN (US); Brian J. Edquist, San Francisco, CA (US); Steven N. Willard, Bloomington, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 721 days.

(21) Appl. No.: 13/392,619

(22) PCT Filed: Aug. 20, 2010

(86) PCT No.: PCT/US2010/002290
§ 371 (c)(1),
(2), (4) Date: Jul. 26, 2012

(87) PCT Pub. No.: WO2011/025528
PCT Pub. Date: Mar. 3, 2011

(65) Prior Publication Data
US 2012/0283770 A1  Nov. 8, 2012

Related U.S. Application Data

(60) Provisional application No. 61/238,297, filed on Aug. 31, 2009.

(51) Int. Cl.
*A61B 17/00* (2006.01)

(52) U.S. Cl.
CPC .. *A61B 17/0057* (2013.01); *A61B 2017/0065* (2013.01); *A61B 2017/00601* (2013.01);
(Continued)

(58) Field of Classification Search
CPC .......... A61B 17/12022; A61B 17/1204; A61B 17/12109; A61B 17/12159; A61B 17/0057;
(Continued)

(56) References Cited

U.S. PATENT DOCUMENTS

| 5,179,963 A | 1/1993 | Berger |
| 6,045,569 A | 4/2000 | Kensey et al. |

(Continued)

FOREIGN PATENT DOCUMENTS

| WO | 2005013832 A1 | 2/2005 |
| WO | 2006093970 A1 | 9/2006 |

OTHER PUBLICATIONS

PCT International Search Report for International Application No. PCT/US2010/002290, mailed Dec. 6, 2010.

*Primary Examiner* — Kathleen Holwerda
*Assistant Examiner* — Socrates L Boutsikaris
(74) *Attorney, Agent, or Firm* — Holland & Hart

(57) ABSTRACT

A tissue puncture locator device includes a temporary anchor configured for placement through a vascular puncture into a vessel. The temporary anchor includes a column member that defines a lumen. The temporary anchor is movable between an uncompressed position and a compressed position, wherein in the compressed poition a portion of the column member protrudes radially outward. The column member may include a reduced thickness portion, wherein the column member protrudes radially outward at the reduced thickness portion. The column member, when expanded radially outward within the vessel, is sized to limit retraction of the temporary anchor through the vascular puncture.

18 Claims, 19 Drawing Sheets

(52) U.S. Cl.
CPC ............ *A61B 2017/00623* (2013.01); *A61B 2017/00654* (2013.01); *A61B 2017/00672* (2013.01)

(58) Field of Classification Search
CPC  A61B 2017/00637; A61B 2017/00654; A61B 2017/00004; A61B 2017/00672; A61B 2017/00659; A61B 2017/00575
USPC .................. 606/213, 192–198, 185; 604/174
See application file for complete search history.

(56) References Cited

U.S. PATENT DOCUMENTS

| | | | |
|---|---|---|---|
| 6,090,130 A | 7/2000 | Nash et al. | |
| 2005/0033360 A1 | 2/2005 | Sing et al. | |
| 2006/0116635 A1 | 6/2006 | Van Heugten et al. | |
| 2009/0030450 A1* | 1/2009 | Preinitz et al. | ............... 606/213 |
| 2009/0171281 A1 | 7/2009 | Pipenhagen et al. | |

* cited by examiner

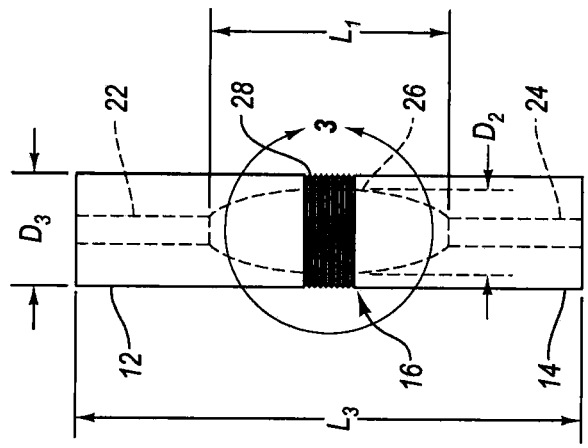
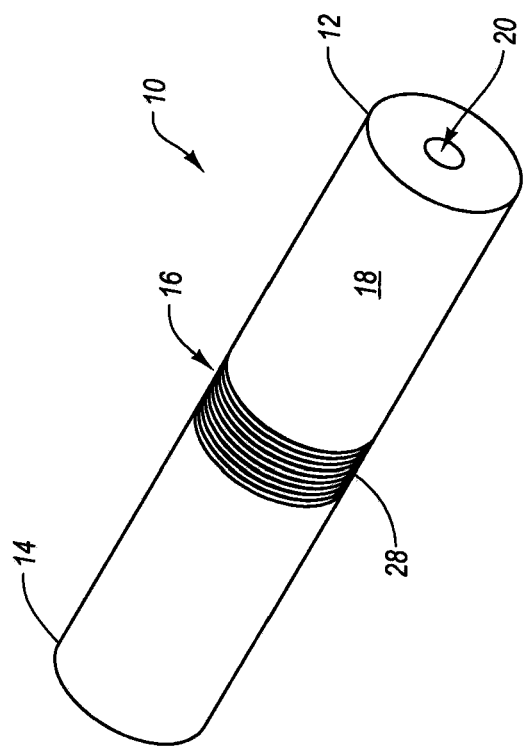

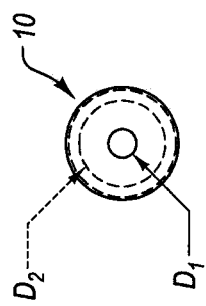
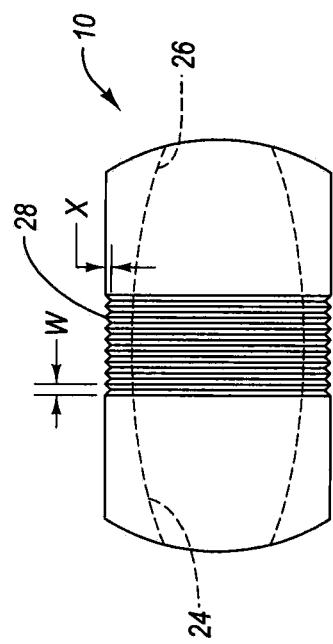

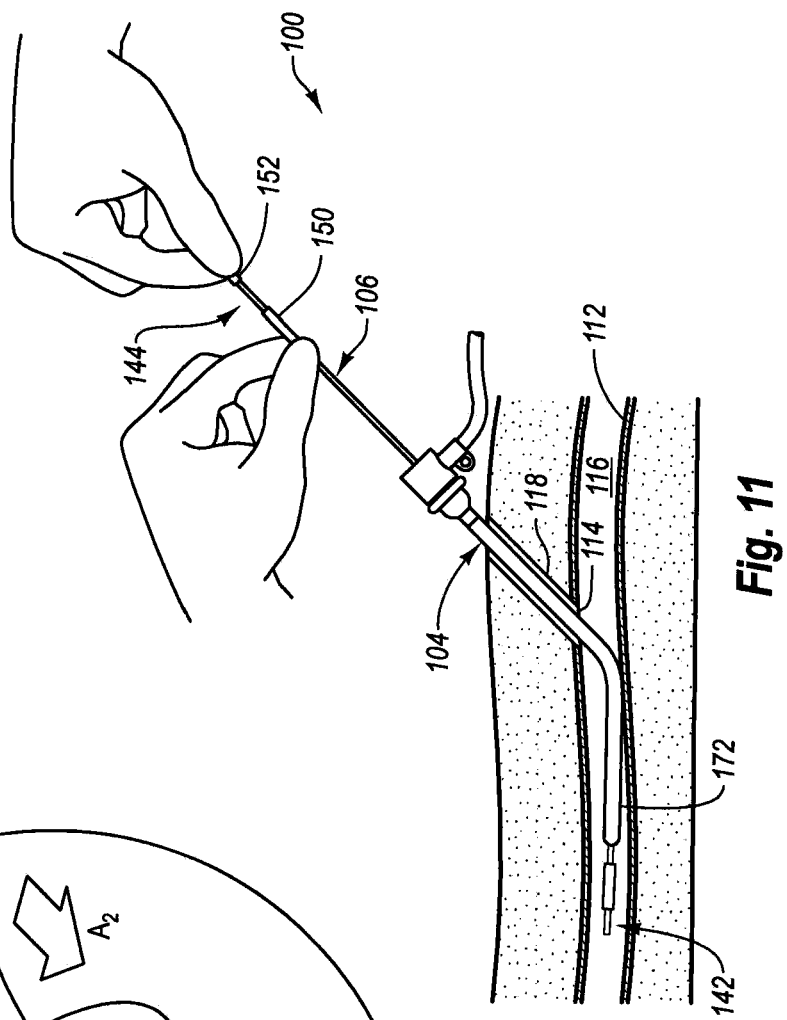
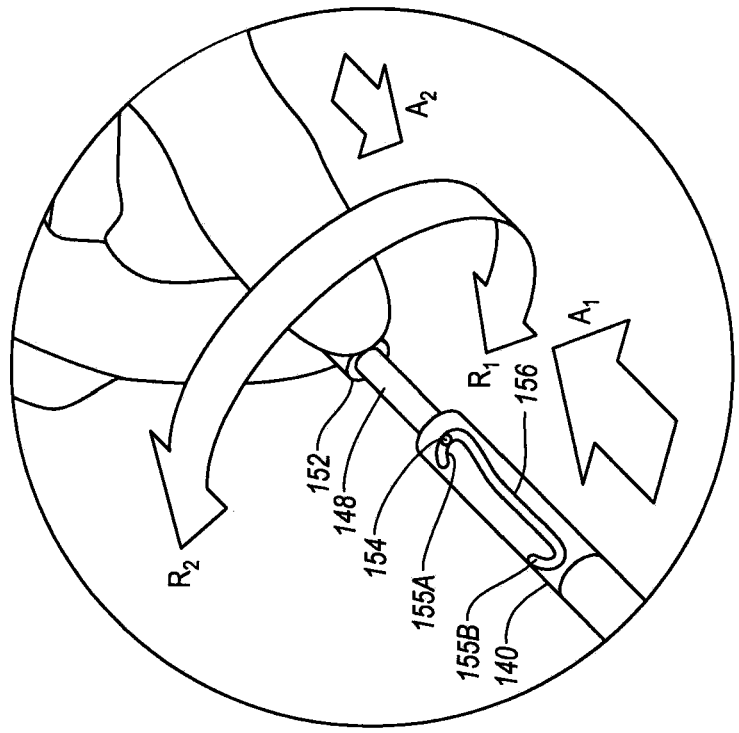
Fig. 11
Fig. 11A

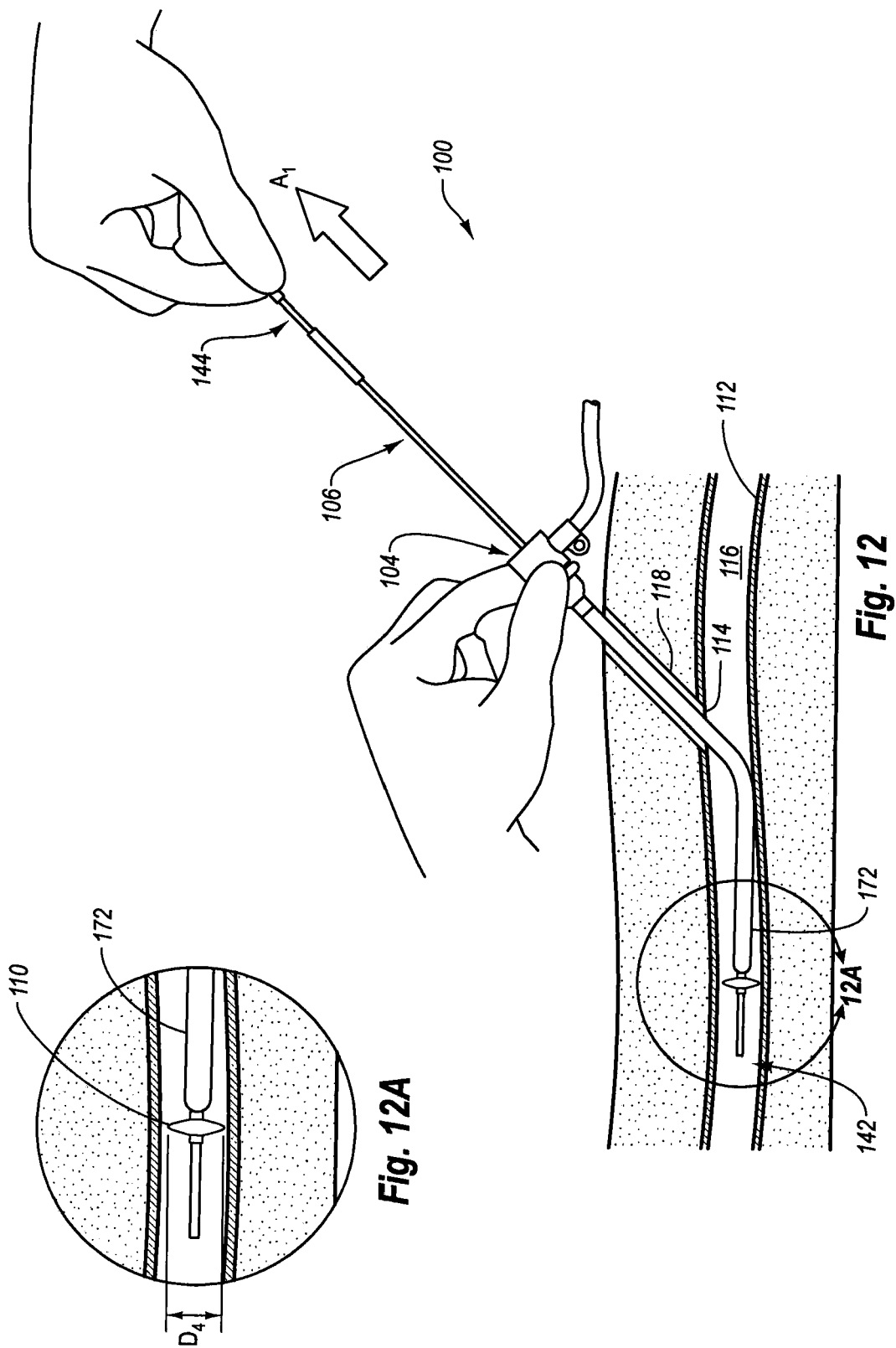

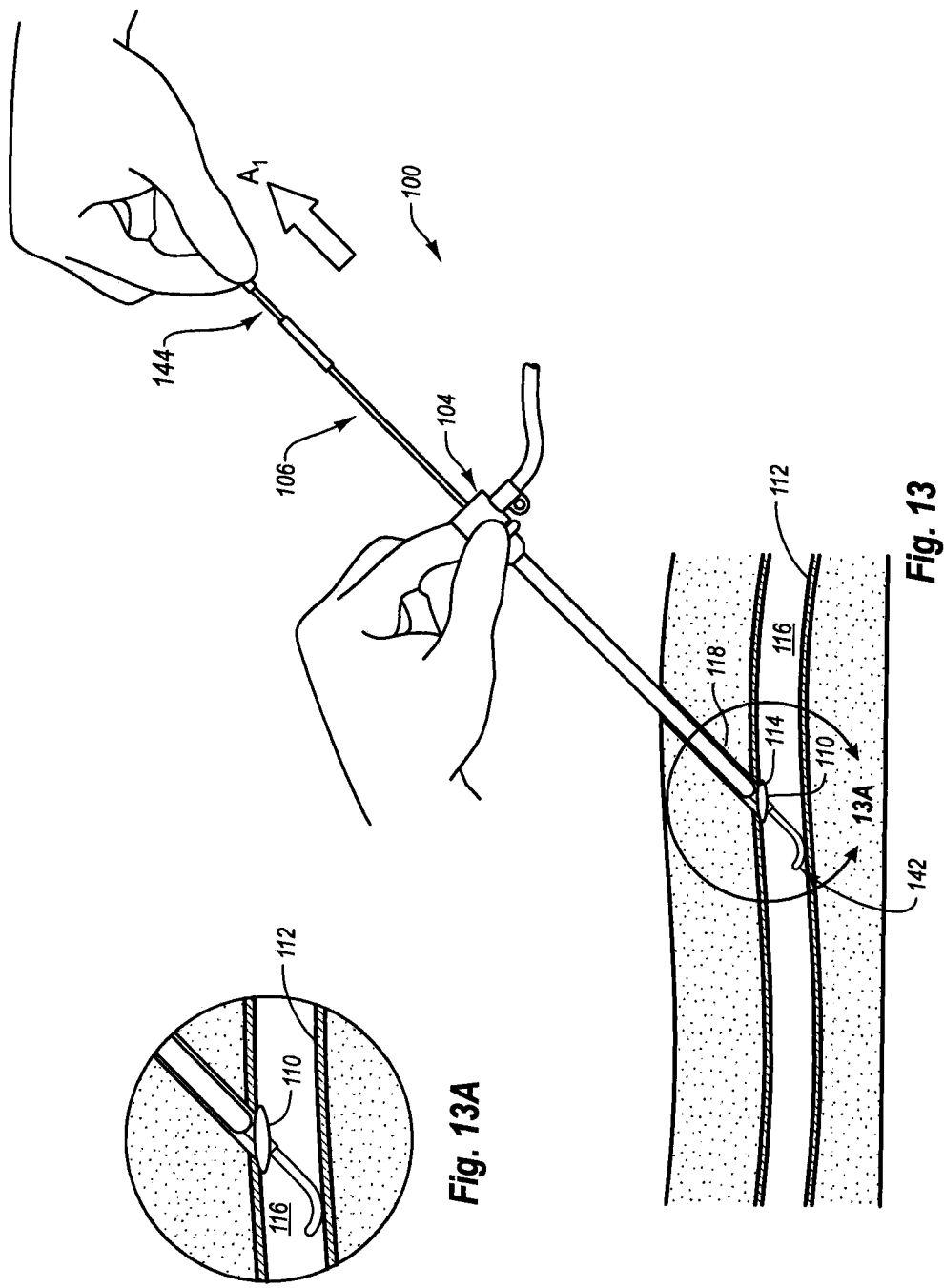

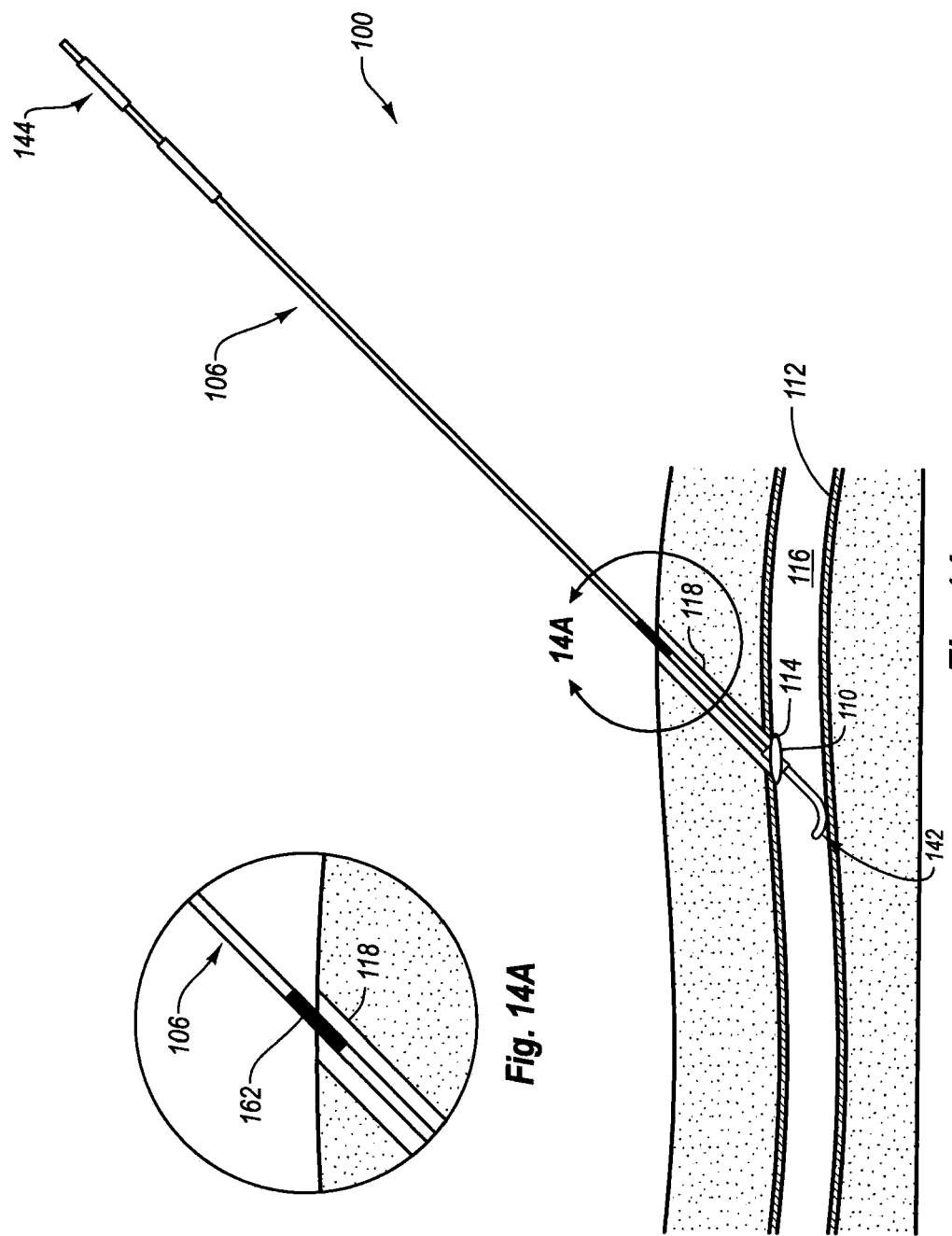

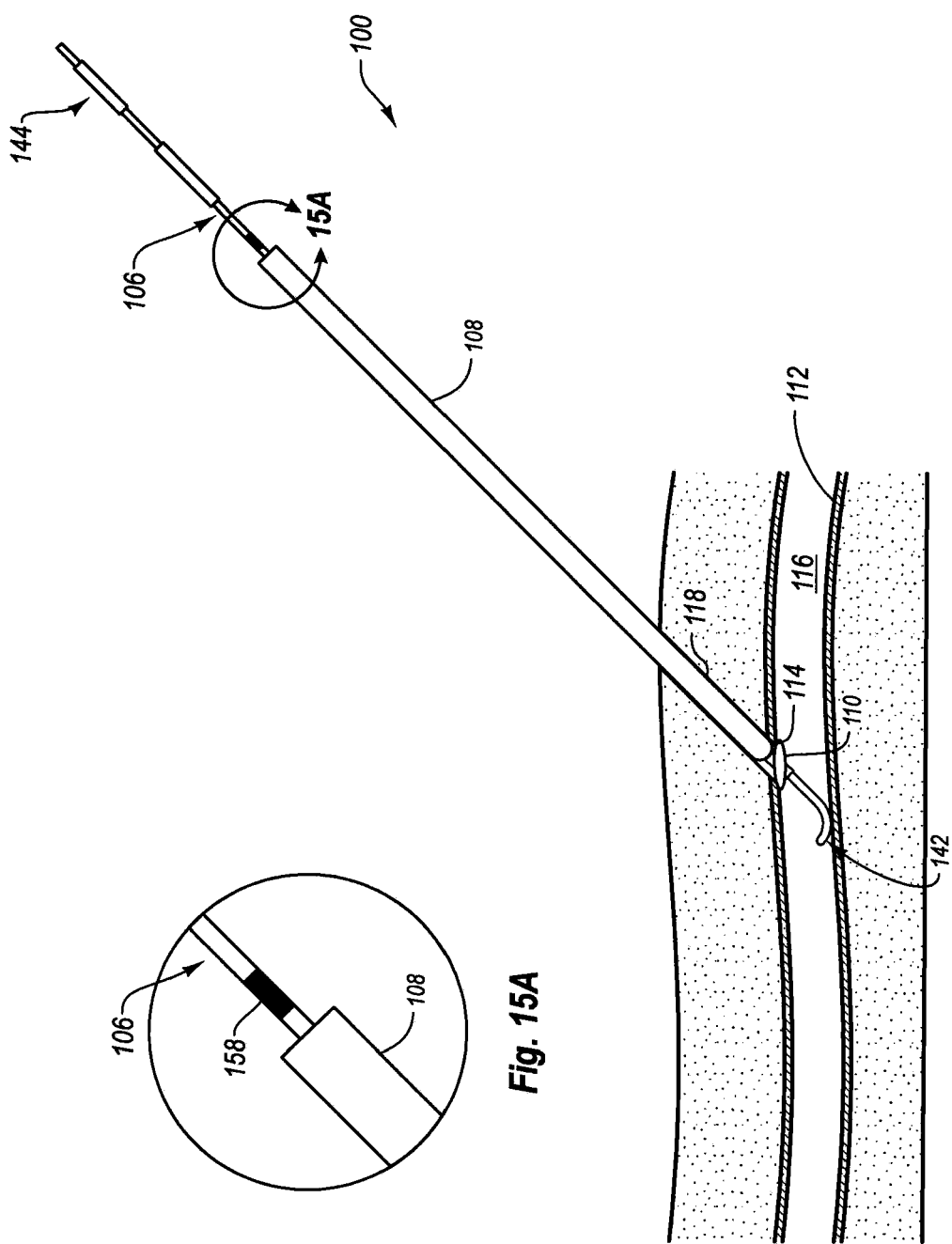

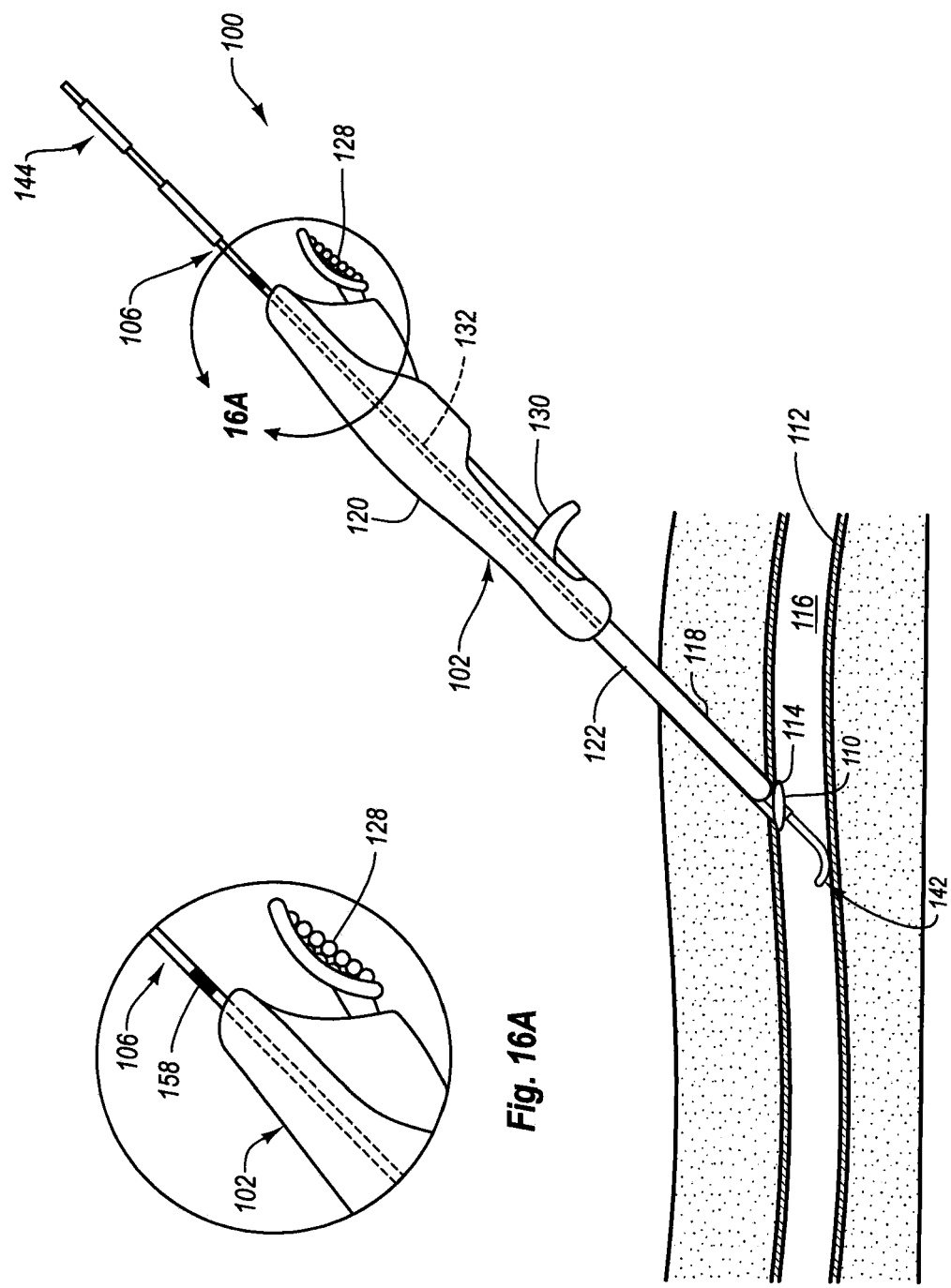

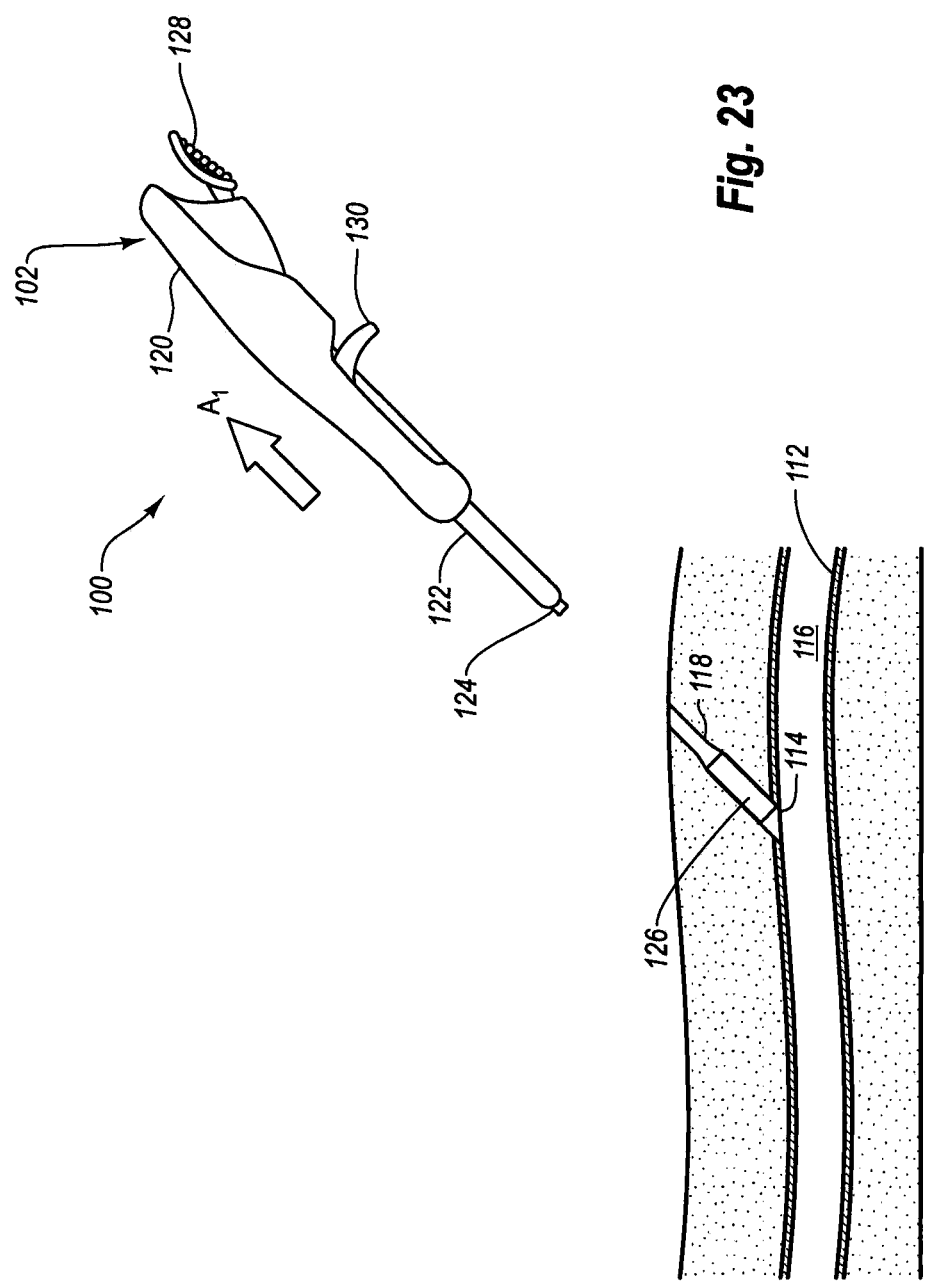

COMPRESSIBLE ARTERIOTOMY LOCATOR FOR VASCULAR CLOSURE DEVICES AND METHODS

RELATED APPLICATION

This application claims the benefit of U.S. Provisional Patent Application No. 61/238,297, filed Aug. 31, 2009, which is hereby incorporated by reference herein in its entirety.

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place a sealing plug at the tissue puncture site. Successful deployment of the sealing plug includes ejection from within the closure device sheath to a location in alignment with and adjacent to the tissue puncture along an outer surface of the vessel. Misalignment of the sealing plug relative to the tissue puncture may result in improper sealing of the tissue puncture. Failure to contact the sealing plug against the outer surface of the vessel can also result in an improper seal.

In extra vascular devices there is no intravascular component used to create a compressive sealing force between the inner wall of the artery and the exterior device. Without an opposite applied force from within the vessel, it may be difficult to place the sealing plug in alignment with the tissue puncture and obtain a proper seal. Some extra vascular devices use staples and resorbable components to seal a tissue puncture but do not utilize a compressive force to press the sealing plug against the tissue puncture since there is no opposing structure inside of the artery against which to apply the compressive force. Staples may be used to stab into the tissue adjacent to the tissue puncture to hold the sealing plug in place. Other types of devices use resorbable components such as collagen plugs that use the radial force of the collagen as it swells to hold the sealing plug in place adjacent to the tissue puncture. Such devices have proven to be less effective in placing a sealing plug adjacent to a tissue puncture and maintaining the sealing plug to provide a proper seal.

SUMMARY

One aspect of the present disclosure relates to a tissue puncture locator device that includes a temporary anchor configured for placement through a vascular puncture and into a vessel. The temporary anchor includes a column member that defines a lumen. The temporary anchor is movable between an uncompressed position and a compressed position, wherein in the compressed position a portion of the column member expands radially outward within the vessel to a size that limits retraction of the anchor through the vascular puncture.

The tissue puncture locator device may further include a compression member adapted for operation outside of the patient to move the temporary anchor between the uncompressed and compressed positions. The uncompressed position permits passage of the temporary anchor through the vascular puncture. The column member may comprise an elastic material such as a polymer material. The tissue puncture locator device may further comprise a sealing member configured for placement adjacent to the vascular puncture along an outer surface of the vessel. The uncompressed position permits passage of the temporary anchor through the sealing member after placement of the sealing member adjacent to the vascular puncture.

The column member may include a reduced thickness portion. The reduced thickness portion may include a concave recess formed in a surface of the lumen of the column member. The concave recess may be annular. The reduced thickness portion may include at least one recess formed in an outer surface of the column member. The at least one recess in the outer surface may be annular. The reduced thickness portion may be molded into the column member.

Another aspect of the present disclosure relates to a tissue puncture closure device adapted for partial insertion into and sealing of a tissue puncture in an internal tissue wall accessible through a percutaneous incision. The device includes a temporary anchor disposed on a distal side of the internal tissue wall. The temporary anchor may include a column structure having a reduced wall thickness portion at a location along a length of the column structure. The temporary anchor has a compressed state (also referred to as a "compressed position") wherein the column structure expands radially outward at the reduced thickness portion to limit movement through the tissue puncture, and an uncompressed state (also referred to herein as an "uncompressed position") wherein the temporary anchor is configured to move through the tissue puncture.

The column structure may define a lumen along at least a portion of a length of the column structure. The reduced wall thickness portion may include a recess formed in a surface of the lumen. The tissue puncture closure device may further include a recess formed in an outer surface of the column structure in radial alignment with the reduced thickness portion. The tissue puncture closure device may further include a compression member arranged and configured to move the temporary anchor between the compressed and uncompressed states. The temporary anchor may be configured to occlude blood flow through the tissue puncture when in the compressed state.

A further aspect of the present disclosure relates to a method of locating a tissue puncture in an internal tissue wall accessible through a percutaneous incision using a temporary anchor. The temporary anchor includes a hollow cylindrical member. The method may include inserting the temporary anchor into the percutaneous incision, applying an axially directed force to the temporary anchor to radially expand a portion of the hollow cylindrical member, and retracting the temporary anchor proximally until the radially expanded portion of the hollow cylindrical member contacts a surface of the internal tissue wall.

Further aspects of the example method include applying a compression force to the temporary anchor in a distal direction. The temporary anchor may include a reduced thickness portion at a location along a length of the hollow cylindrical member, wherein radially expanding a portion of the hollow cylindrical member includes radially expanding the reduced thickness portion. The temporary anchor may further include a recess formed in the hollow cylindrical member along an internal surface thereof.

Additional advantages and novel features will be set forth in the description which follows or can be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not limit the scope of the invention.

FIG. 1 is a perspective view of an example arteriotomy locator column member in an unexpanded state in accordance with the present disclosure.

FIG. 2 is a side view of the column member shown in FIG. 1.

FIG. 3 is an enlarged partial view of the column member of FIG. 2.

FIG. 4 is an end view of the column member of FIG. 1.

FIG. 10 and 10A are side views of the tissue puncture treatment assembly of FIG. 9 with the locator wire inserted into the introducer and into the vessel.

FIGS. 11 and 11A are side views of the tissue puncture treatment assembly of FIG. 10 with a column member of the locator wire being expanded.

FIGS. 12 and 12A are side views of the tissue puncture treatment assembly of FIG. 11 with the locator wire being retracted to engage the expanded column member against a distal end of the introducer.

FIGS. 13 and 13A are side views of the tissue puncture treatment assembly of FIG. 12 with the introducer and locator wire being retracted to engage the expanded column member against an interior wall of the vessel.

FIGS. 14 and 14A are side views of the tissue puncture treatment assembly of FIG. 13 with the introducer removed.

FIGS. 15 and 15A are side views of the tissue puncture treatment assembly of FIG. 14 with a tissue tract dilator advanced over the locator wire and into a percutaneous incision.

FIGS. 16 and 16A are side views of the tissue puncture treatment assembly of FIG. 15 with the tissue tract dilator removed and a sealing pad delivery device advanced over the locator wire and into the percutaneous incision.

FIGS. 21 and 21A are side views of the tissue puncture treatment assembly FIG. 20 with the locator wire being actuated to move the column member into an unexpanded state.

FIG. 23 is a side view of the tissue puncture treatment assembly of FIG. 22 with the sealing pad delivery device removed from the percutaneous incision.

Throughout the drawings, identical reference numbers designate similar, but not necessarily identical, elements.

DETAILED DESCRIPTION

Figure 7:
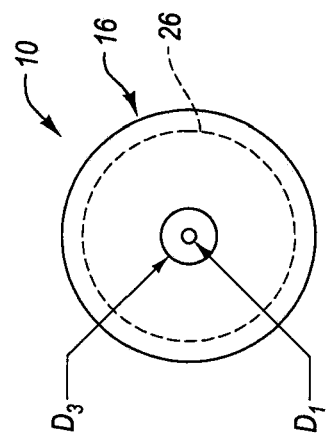
FIG. 7 is an end view of the expanded column member of FIG. 5.

As mentioned above, vascular procedures are conducted throughout the world and require access to an vessel through a puncture. Most often, the vessel is a femoral artery. To close the puncture following completion of the procedure, many times a closure device is used to position a sealing plug within a percutaneous incision adjacent to the puncture. Orientation of the sealing plug relative to the puncture may be particularly useful for successful sealing of the puncture.

An anchor positioned within the vessel may provide a sealing or partial sealing function for the puncture prior to disposing the sealing plug adjacent to the puncture. The anchor may be constructed and positioned within the vessel to at least partially block or occlude a flow of blood through the puncture.

An anchor positioned within the vessel may also act as a locator or reference point during placement of the sealing plug relative to the puncture. The anchor is positioned adjacent the puncture on an internal wall of the vessel. The sealing plug is then deposited adjacent to the puncture on an outer wall of the vessel. Proper positioning of the sealing plug relative to the puncture may be particularly difficult without an anchor provided internal the vessel that provides a locator or reference point function.

In some puncture sealing procedures, compressing the sealing plug against the puncture may improve sealing of the puncture. In order to apply a compressing force to the sealing plug, it may be helpful to provide an anchor positioned within the vessel on an opposite side of the vascular wall from the sealing plug. The anchor may be held against the interior surface of the vessel wall as the sealing member is compressed in the distal direction against an exterior surface of the vessel wall to create a seal against the outer surface of the vessel in the area adjacent to the puncture.

Some types of anchors for use with closure devices include a mechanical expansion member. This type of anchor includes a membrane that is expandable or at least deformable within the vessel upon opening of the mechanical expansion member within the membrane. The mechanical expansion member may include a plurality of metal spoke, rods, or link members that are actuatable from a contracted position for passage through the puncture, to a radially outward expanded position within the membrane while positioned within the vessel. When the expansion member is in the expanded position within the vessel, the expansion member and membrane together function as an anchor within the vessel for the closure device.

Anchors that include mechanical expansion members as discussed above may be complex and difficult to manufacture and assembly due to the expansion and contraction functions that are required and the relatively small size of the expansion member features. Further, such anchors may be costly to manufacture because of, for example, the metal materials used and the difficulties in creating the necessary shapes and assembly of parts.

The example closure devices described with reference to the attached figures include a temporary anchor member that is operable without the use of a mechanical expansion member or a membrane. The term "temporary" as used herein related to the anchor member is defined as an anchor that lasts for a limited time. The temporary anchor member is maintained in the vessel for a limited time and then manually removed from the vessel. A temporary anchor may be different from anchor members that are deposited and left in the vessel. In some cases, these alternative types of anchor members comprise a bioresorbable material that is absorbed into the body over time.

In one arrangement, the temporary anchor member includes a compressible column structure. The compressible column structure includes a reduced thickness portion at a location between distal and proximal ends of the column structure. The column structure protrudes radially outward in the area of the reduced thickness portion upon application of an axially applied compression force. The radially outward protruding portion of the column structure provides an anchor that limits proximal movement of the anchor through the tissue puncture. In at least some examples, the compressible column structure includes an elastic material that returns to its original shape after removal of the axially applied compression force.

While the vascular instruments shown and described below include procedure sheaths and puncture closure devices, the application of principles described herein are not limited to the specific devices shown. The principles described herein may be used with any medical device. Therefore, while the description below is directed primarily to vascular procedures and certain embodiments of a vascular closure device. However, the general principles related to vascular puncture locators may be applicable to other devices and procedures outside of vascular closure devices and the placement of sealing plugs.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engagable" are also used broadly to mean interlock, mesh, or contact between two devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

FIGS. 1-4 illustrate example arteriotomy locator column member 10 for the use with a tissue puncture treatment assembly as will be described in further detail below. The arteriotomy locator column member 10 (referred to as "column member" or "compressible column member" throughout) includes first and second end portions 12, 14, and an expandable portion 16 located between the first and second end portions 12, 14. The column member 10 also has an outer side surface 18 and an aperture or lumen 20 that extends from the first end portion 12 to the second end portion 14.

The aperture 20 may include a first end portion 22, a second end portion 24, and a central portion 26 (see FIG. 2). The first and second end portions 22, 24 are shown having the same maximum diameter or dimension $D_1$. In some arrangements, the dimension $D_1$ may be different at each of the first and second end portions 22, 24.

The central portion 26 has a maximum diameter or dimension $D_2$. Typically, the dimension $D_2$ is greater than the dimension $D_1$. The aperture 20 may taper gradually (e.g., a contoured taper or a linear taper) from the dimension $D_1$ to the dimension $D_2$. Alternatively, the aperture 20 may include, for example, at least one step feature between the dimensions $D_1$ and $D_2$. The greater dimension $D_2$ provides a smaller material thickness along the expandable portion 16 as compared to the material thickness of the column member along the first and second end portions 12, 14. The thinner material thickness in the area of expandable portion 16 provides collapsibility of the column member 10, wherein the expandable portion 16 expands radially outward relative to the first and second end portions 12, 14.

Figure 5:
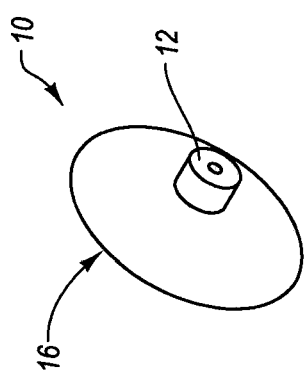
FIG. 5 is a perspective view of the column member of FIG. 1 in an expanded state.
Figure 6:
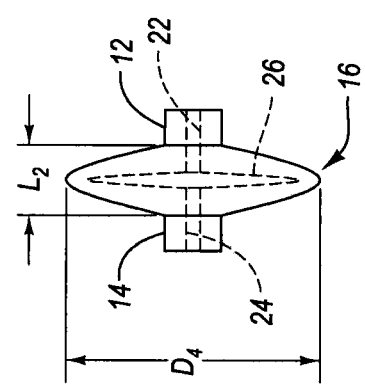
FIG. 6 is a side view of the expanded column member of FIG. 5.

FIGS. 5-7 illustrate the column member 10 in an expanded state or axially compressed state with the expandable portion 16 expanded radially outward. When the column member 10 is in an unexpanded state as shown in FIGS. 1-4, the expandable portion 16 has a length L, and the column member 10 has a total length $L_3$. In the expanded state shown in FIGS. 5-7, the expandable portion 16 has a length $L_2$.

The column member 10 in an unexpanded state shown in FIGS. 1-4 has a relatively constant outer diameter or dimension $D_3$. In the expanded state, the expandable portion 16 of the column member 10 has a maximum diameter or dimension $D_4$ as shown in FIGS. 6 and 7. Typically, the dimension $D_4$ is greater than a maximum width dimension of a tissue puncture being treated by the tissue puncture treatment assembly of which the column member 10 is a component. The diameter $D_3$ is typically smaller than the maximum width dimension of the tissue puncture 114 to permit insertion of the column member through the tissue puncture when the column member is in an unexpanded state. The dimension $D_3$ is also typically smaller than an internal dimension of an introducer through which the column member 10 is inserted into the vessel.

The column member 10 may further include a plurality of outer surface recesses 28 defined along the outer side surface 18. The recesses 28 may have a depth X and a width W (see FIG. 3). The recesses 28 may extend around an entire periphery of the column member along the outer side surface 18. In some arrangements, only a single recess 28 is positioned along the outer side surface 18. The recesses 28 may be generally circular. Alternatively, the recesses 28 may have a helical shape or any other desired shape, size, or arrangement along the outer side surface 18.

The outer surface recesses 28 may further reduce a thickness of the column member in the area of the expandable portion 16. The recesses 28 may be constructed and arranged to reduce the amount of force applied in an axially direction to the column member 10 needed for the expandable portion to collapse into the expanded orientation shown in FIGS. 5-7.

In some arrangements, the outer surface recesses 28 may be substantially eliminated when the expandable portion 16 moves into the expanded state shown in FIGS. 5-7 as the material that defines the expandable portion 16 elastically deforms, thereby flattening the recesses 28. As clearly shown in FIGS. 1-4 and 5-7, the recesses 28 are formed in an outer surface that is continuous around a circumference or perimeter of the column member 10.

Figure 8:
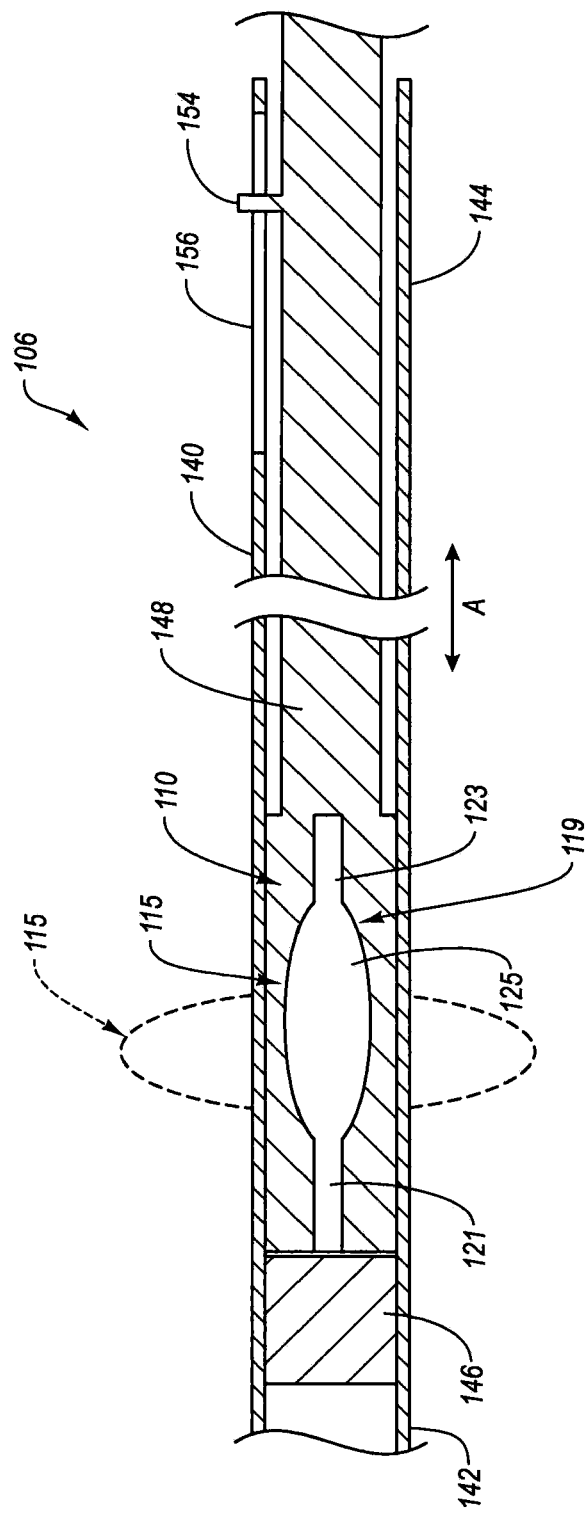
FIG. 8 is a cross-sectional view of a portion of a locator wire having an arteriotomy locator column member in accordance with the present disclosure.

The column member 10 or other column member constructions with similar features as described above with reference to FIGS. 1-7 may be used with a locator wire that is a component of a tissue puncture treatment assembly, as will be described in further detail below. An example locator wire 106 is shown in FIG. 8. The locator wire 106 includes a column member 110 having an expandable portion 115. The column member 110 further includes an aperture 119 having a distal end 121, a proximal end 123, and a central portion 125. The column member 110, when compressed by application of an axially applied force in the direction A, expands radial outward into an expanded state (i.e., see the broken line version of expanded portion 115 in FIG. 8).

The locator wire 106 includes a locator tube 140 that extends from a distal end portion 142 to a proximal end portion 144. A plug 146 is positioned at the distal end portion 142 distal of the column member 110 to limit movement of the column 110 in the distal direction within the locator tube 140. The locator wire 106 may further include a compression member 148 that extends from the proximal end portion 144 distally to the column member 110. A follower member 154 may extend radial outward from the compression member 148 at a location proximal of the column member 110. A track 156 may be defined in a side wall of the locator tube 140 within which the follower member 154 tracks. Movement of the follower member 154 within the track 156 may alter an orientation of the compression member 148 relative to the locator tube 140.

In at least in one example, the column member 110 may be compressed into an expanded state by moving the compression member 148 in the distal direction while the follower member 154 follows within the track 156. The track 156 may include locking portions 155A, 155B that help lock the compression member 148 in a given axial position relative to the locator tube 140. In one example, the locking portion 155A retains the compression member 148 in a position advanced distally relative to the locator tube 140, wherein the column member 110 is compressed to create the expanded state shown in broken line in FIG. 8.

In one example, the locator wire 106 may be used to both locate a vessel puncture and to achieve and maintain temporary hemostatis. The column member 110 is a feature of the locator wire 106 that is inserted into a vessel via a procedural introducer. Due to the limited inner diameter of the introducer and the size of the vessel puncture, the column member 110 and the distal end portion 142 of the locator wire 106 also has a relatively small outer dimension to permit advancement of the locator wire 106 through the introducer and into the vessel.

Once the column member is positioned inside the vessel and extending beyond a distal end of the introducer, the column member may be expanded radially (i.e., the expanded state show in FIGS. 5-7) such that the column member has a maximum dimension that is larger than the maximum size of the puncture and the inner diameter of the introducer. The locator wire is then retracted proximally until the expanded column member engages the distal end of the introducer. The introducer and locator wire are together retracted proximally until the expanded column member is engaged against an inner surface of the vessel. Engaging the expanded column member against the inner surface of the vessel adjacent to the vessel puncture may provide hemostasis as well as provide an anchor function. Typically, the column member comprises sufficient tactile and structural rigidity so that the expanded column member does not inadvertently retract through the vessel puncture and out of the vessel.

The column member positioned a distal end of the locator wire may be axially compressed using an actuator such as a plunger (i.e., the compression member 148) causing the column member to axially compress and expand radially outward. The column member may expand radially outward through an opening defined along the locator wire such as along an exterior surface of a locator tube 140. In other arrangements, a portion of the locator tube expands radially outward with the radially outward expansion of the column member. The actuator may be locked in an axially advanced position to maintain compression forces on the column member that provide radially outward expansion, and later released to permit the column member to regain its original unexpanded shape. In some arrangements, the column member includes elastic material that facilitates the radially outward expansion of the column member to provide temporary hemostasis and anchoring for tissue puncture treatment assembly, and then return of the column member to its original unexpanded shape that permits retraction through the vascular puncture. The column member in its unexpanded state may have a smaller outer profile (e.g., width or diameter) than other types of locator or anchor member such as, for example, an expandable frame member that is covered by a flexible membrane. The smaller profile of the column member which results at least in part from elimination of an expandable frame structure has the potential to reduce the overall size of the locator that must be removed through at least a portion of the deployed sealing pad in the percutaneous incision.

Typically, the column member comprises a polymeric material that has elastic properties. Many polymeric and non-polymeric elastic materials may be used, including, for example, polyurethane, silicone, polyvinyl chloride, and rubber based materials. Referring now to FIGS. 9-23, an example tissue puncture treatment assembly 100 is described with reference to treatment of a vessel puncture 114. The tissue puncture treatment assembly 100 is merely exemplary of the many devices that could utilize the various compressible column structures disclosed herein. The functionality, features, and methods of use described herein with reference to FIGS. 9-23 represent one application of the compressible column structures disclosed herein in a tissue puncture treatment device. Other applications are possible.

The tissue puncture treatment assembly 100 includes a sealing pad delivery device 102, an introducer 104, a locator wire 106 (i.e., the locator wire 106 described above in reference to FIG. 8), and a tissue tract dilator 108. The tissue puncture treatment assembly 100 is used to seal closed a vessel puncture 114 that is defined in a vessel 112. The vessel 112 includes a vessel interior 116. The vessel puncture 114 is accessible from outside a patient via a percutaneous incision 118.

Figure 9:
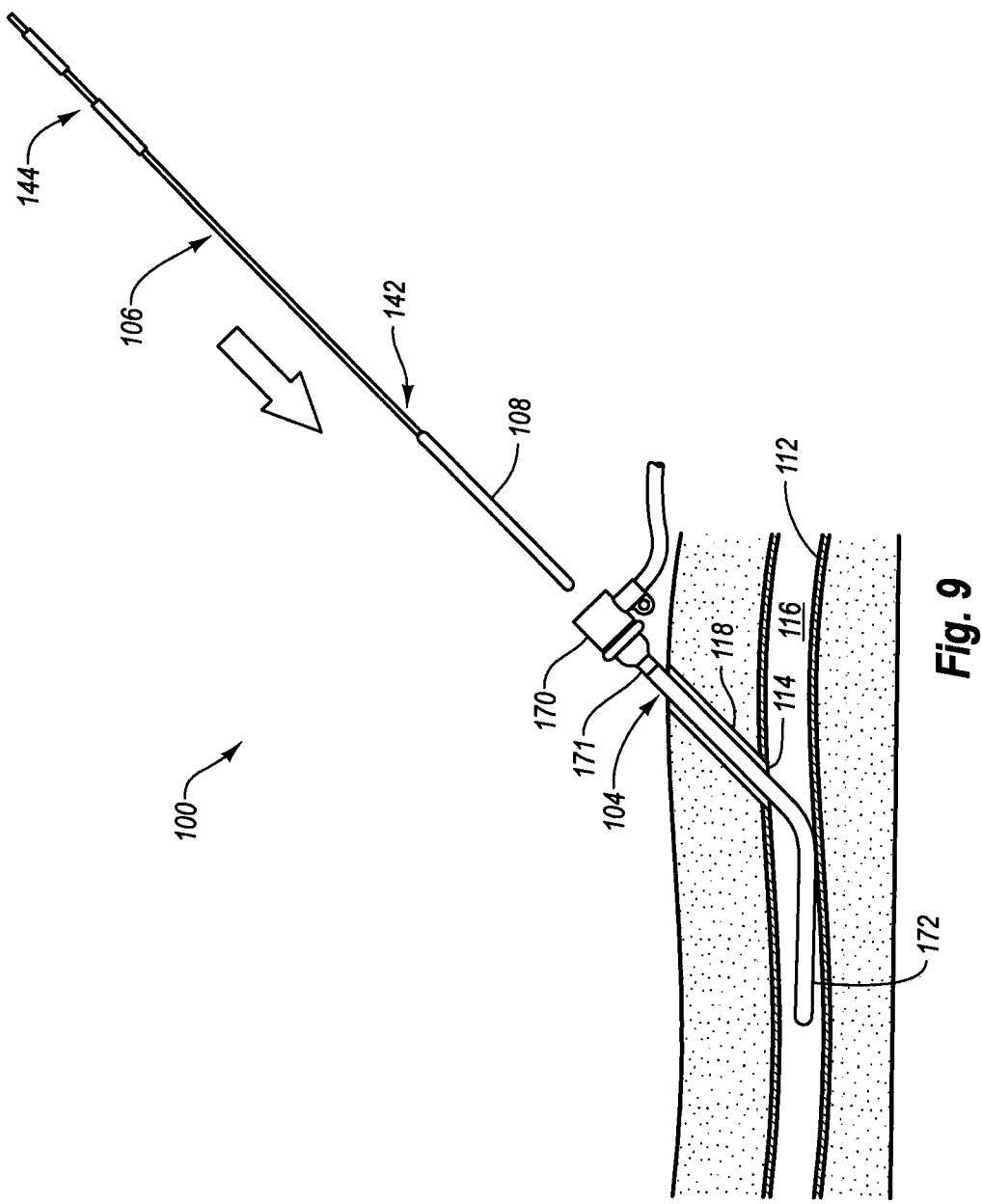
FIG. 9 is a side view of an example tissue puncture treatment assembly in accordance with the present disclosure, wherein the introducer is inserted into a vessel and a locator wire is positioned for insertion into the introducer.

Referring first to FIG. 9, the introducer 104 is inserted through the percutaneous incision 118 and vessel puncture 114 until a distal end 172 of the introducer 104 is positioned within the vessel interior 116. A hub 170 is positioned at proximal end 171 of the introducer 104. The hub 170 defines an opening into the introducer through which the locator wire 106 is advanced. The locator wire 106 includes a distal end portion 142 and a proximal end portion 144. Typically, the distal end portion 142 is advanced through the hub 170 until the distal end portion 142 extends distally beyond the distal end 172 of the introducer.

The tissue tract dilator 108 is advanced over the locator wire 106 after the locator wire has been advanced into the vessel 112. The tissue tract dilator 108 may be used to enlarge at least the percutaneous incision 118 to a size great enough for insertion of a sealing pad into the percutaneous incision 118.

Figure 10:
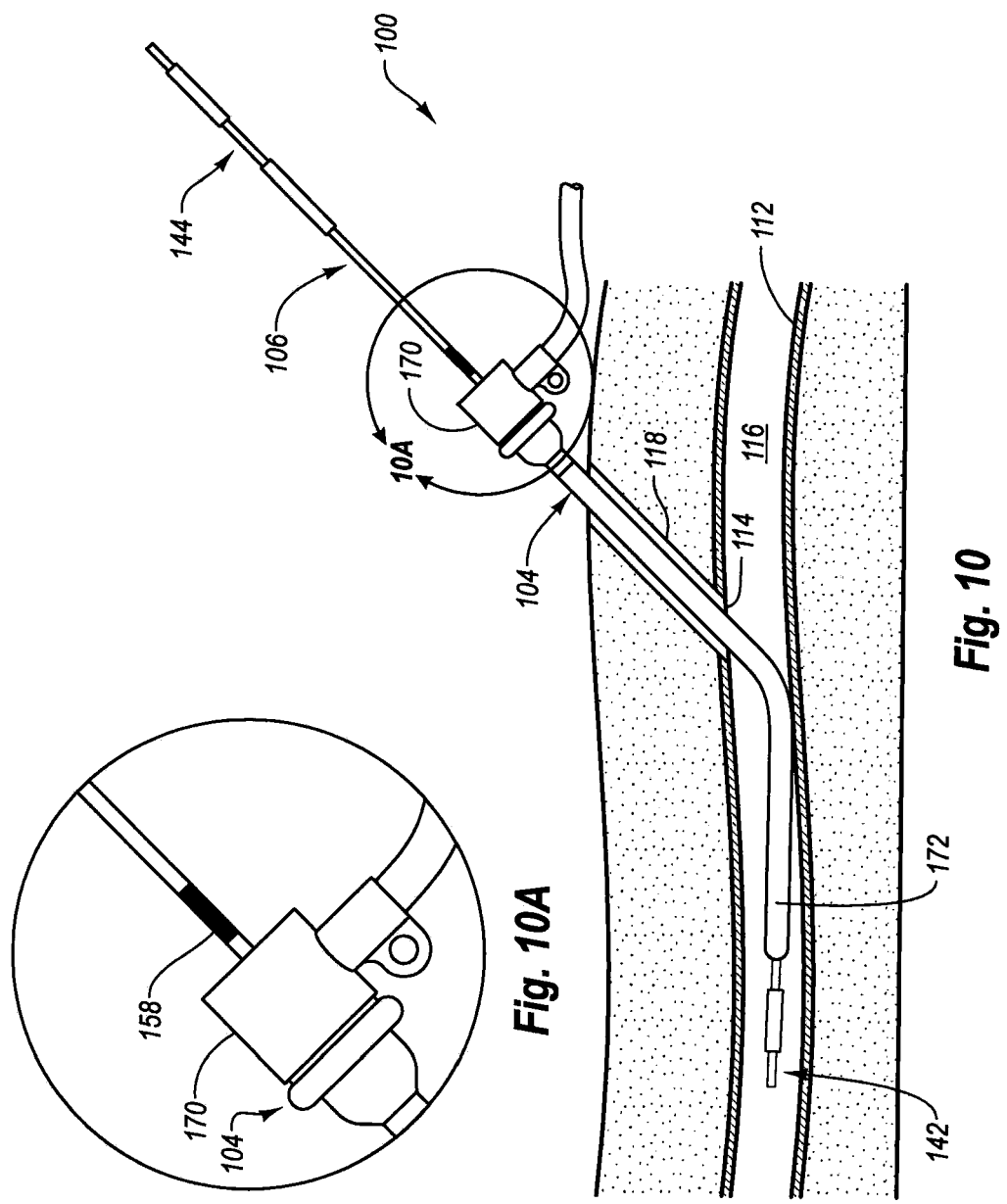

Referring now to FIGS. 10 and 10A, the locator wire 106 is advanced distally through the introducer 104 until the distal end portion 142 is positioned within the vessel interior 116 at a location distal of the distal end 172 of the introducer. Proper positioning of the distal end portion 142 may be confirmed by visualizing a first marker 158 at a location adjacent to the hub 170 as shown in FIG. 10A.

Referring now to FIGS. 11 and 11A, the locator wire 106 is actuated to compress the column member 110 into a radially outward expanded state. In one example, the locator wire 106 includes a compression member 148 that extends through a locator tube 140. A first grasping member 150 is positioned on the locator tube 140, and a second grasping member 152 is positioned on the compression member 148. The follower member 158 extends from an outer surface of the compression member 148. The follower member 154 moves within a track 156 defined in an outer surface of the tube member 140.

The operator rotates the compression member 148 relative to the tube member 140 in the direction $R_1$ to move the follower out of the locking portion 155A of the track 156, then applies an axial force in the direction $A_1$ via the first grasping member 150 while applying a force in the opposite direction $A_2$ to the compression member 148 via the second grasping member 152. When the follower member 154 reaches the distal end of the track 156, the operator applies a rotational force in the direction $R_2$ to lock the follower member 154 within a locking portion 155B of the track 156.

Applying the axial compression forces shown and described with reference to FIGS. 11 and 11A, cause the column member 110 to collapse and expand radially outward as shown in FIGS. 12 and 12A. The column member 110 has a maximum diameter or width dimension $D_4$ when in the expanded state shown in FIG. 12A. Typically, the dimension $D_4$ is greater than a maximum width dimension of the vessel puncture 114. The dimension $D_4$ is also typically greater than an internal dimension of the introducer 104 at the distal end 172. The operator applies a retraction force to locator wire 106 in the proximal direction $A_1$ shown in FIG. 12 to contact the column member 110 against a distal end surface of the introducer 104.

Referring now to FIGS. 13 and 13A, the operator concurrently retracts the introducer 104 and locator wire 106 in the direction $A_1$ until the column member 110 contacts against an inner surface of the vessel 112 adjacent the vessel puncture 114. Typically, the column member 110 provides hemostasis at the vessel puncture 114. The operator should feel a slight resistance to retraction in the direction $A_1$ once the expanded column member 110 contacts against the inner surface of the vessel 112.

Referring to FIGS. 14 and 14A, the operator maintains at least some tension on the locator wire 106 in the direction $A_1$ to maintain hemostasis while removing the introducer 104 in direction $A_1$ from off the locator wire 106. Typically, a second marker 162 is at least partially visible outside of the percutaneous incision 118 after removal of the introducer 104.

Referring now to FIGS. 15 and 15A, a tissue tract dilator 108 may be advanced distally over the locator wire 106 and into the percutaneous incision 118. The tissue tract dilator 108 is advanced distally until the first marker 158 is at least partially visible outside a proximal end of the tissue tract dilator 108. Typically, at least some tension is applied to the locator wire 106 to maintain hemostasis during advancement of the tissue tract dilator 108 into the percutaneous incision 118. The tissue tract dilator 108 may be used in some circumstances when the size or shape or the percutaneous incision 118 is not sufficient for placement of a sealing pad or positioning of the sealing pad delivery device 102.

Referring now to FIGS. 16 and 16A, the tissue tract dilator 108 is removed from percutaneous incision 118 and off from the locator wire 106 in the direction $A_1$. At least some tension is typically applied to the locator wire 106 in the proximal direction $A_1$ while removing the tissue tract dilator 108. The sealing pad delivery device 102 is then advanced distally over the locator wire 106 and into the percutaneous incision 118. Typically, the sealing pad delivery device 102 is advanced distally in the direction $A_2$ until the first marker 158 is at least partially visible at a location proximal of the sealing pad delivery device 102.

The sealing pad delivery device 102 includes a housing 120, a carrier tube 122 extending from a distal end of the housing 120, a positioning tube 124 positioned within the carrier tube 122, and a sealing pad 126 positioned within the carrier tube 122 and located distal of the positioning tube 124. The sealing pad delivery device 102 may also include a wire locking member 128, a tube retracting actuator 130, and a wire aperture 132. The wire aperture 132 extends from a proximal end of the housing 120 to a distal end of the carrier tube 122 and is sized to receive the locator wire 106.

Figure 17:
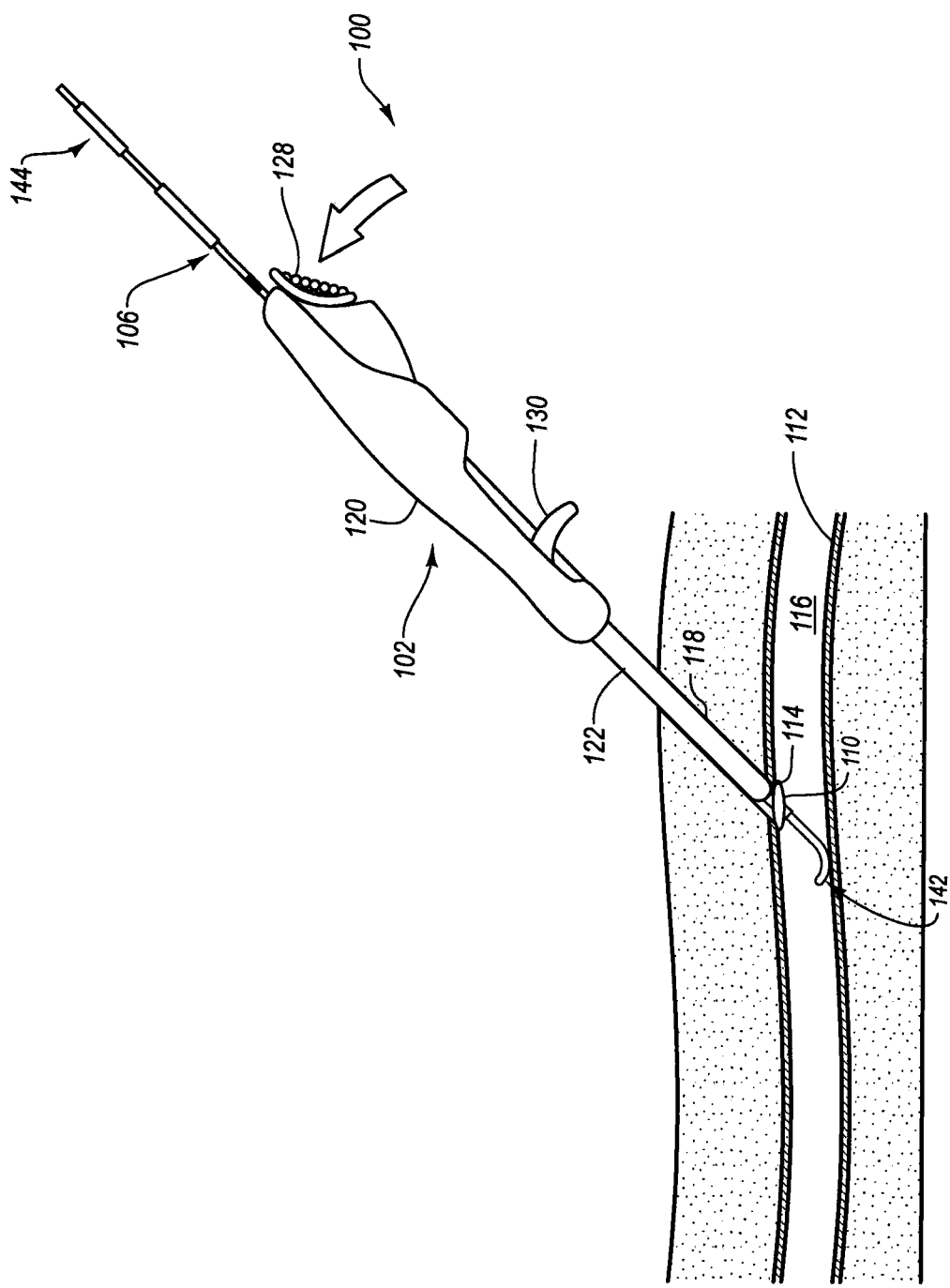
FIG. 17 is a side view of the tissue puncture treatment assembly of FIG. 16 with the sealing pad delivery device locked onto the locator wire.

Referring now to FIG. 17, once the sealing pad delivery device 102 is positioned within the percutaneous incision 118 with the first marker 158 at least partially visible and tension being applied to the locator wire 106, the wire locking member 128 is actuated to fix an axially position of the sealing pad delivery device 102 relative to the locator wire 106. In at least one example, the wire locking member 128 contacts the locator wire 106 directly with a force sufficient to limit movement of the sealing pad delivery device 102 in the axial direction relative to the wire 106 when applying forces that are typical in treating a vessel puncture 114. Many constructions are possible for the wire locking member 128 to provide the desired resistance to relative movement between the sealing pad delivery device 102 and the locator wire 106.

Figure 18:
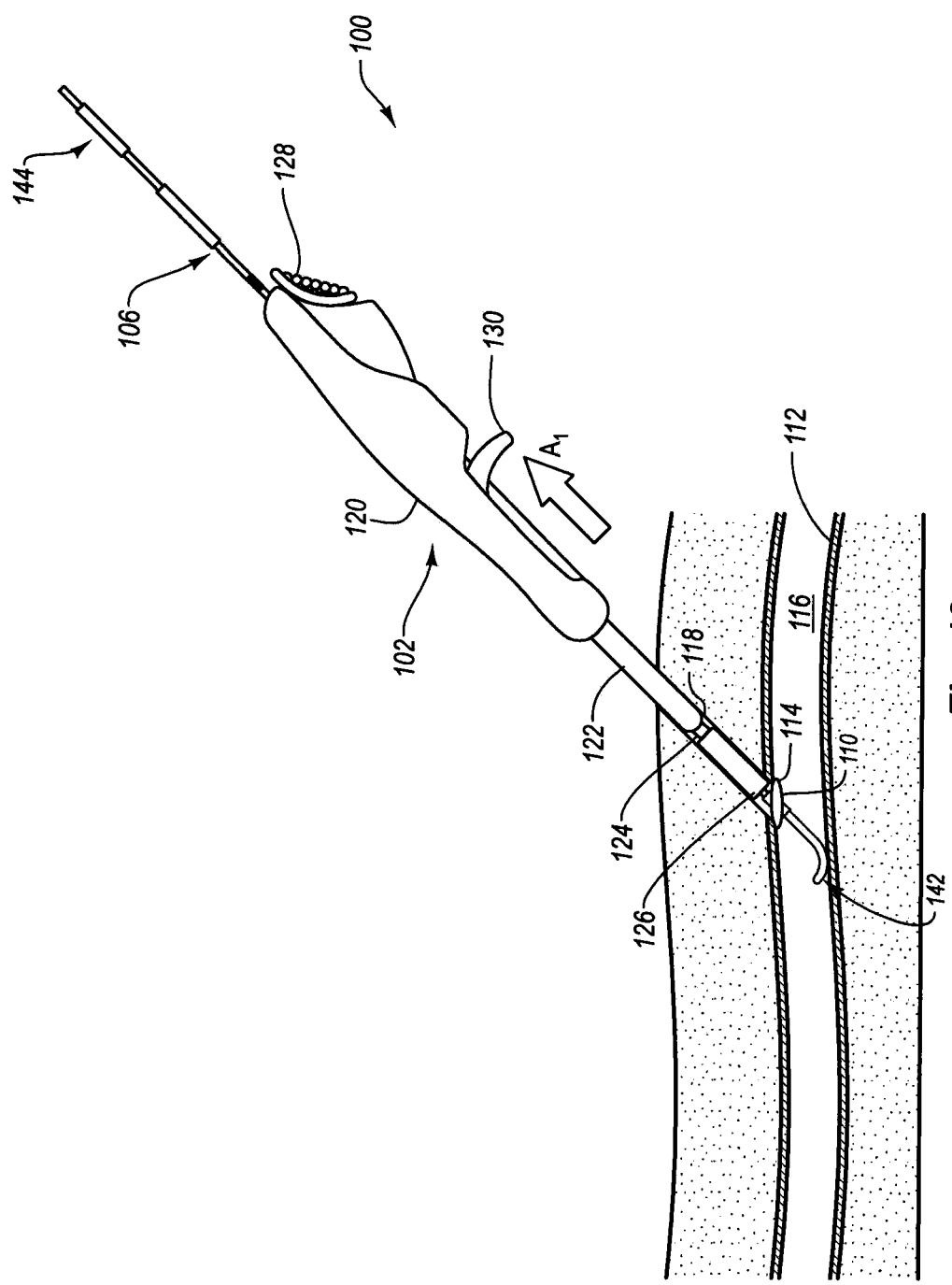
FIG. 18 is a side view of the tissue puncture treatment assembly of FIG. 17 with the sealing pad delivery device actuated to expose a sealing pad within the percutaneous incision.

Referring now to FIG. 18, a force is applied to the retraction actuator 130 in the proximal direction $A_1$ to retract the carrier tube 122 at least partially into the housing 120. Typically, the carrier tube 122 is retracted with the tube retractor actuator 130 a distance sufficient to fully expose the sealing pad 126 within the percutaneous incision 118.

In at least some arrangements, exposing the sealing pad 126 within the percutaneous incision 118 also advances the sealing pad 126 in the distal direction $A_2$. In one example, the positioning tube 124 can be used to distally advance the sealing pad 126. In other arrangements, the positioning tube 124 holds the sealing pad in a fixed position during retraction of the carrier tube 122.

The column member 110, held in contact with the inner surface of the vessel 112 adjacent to the vessel puncture 114, may provide an anchor to resist axial forces applied to the sealing pad 126 in the distal direction $A_2$. The anchor function of column member 110 limits movement of the sealing pad 126 through the vessel puncture 114 and can facilitate some compression of the sealing pad 126 toward the vessel puncture 114.

Figure 19:
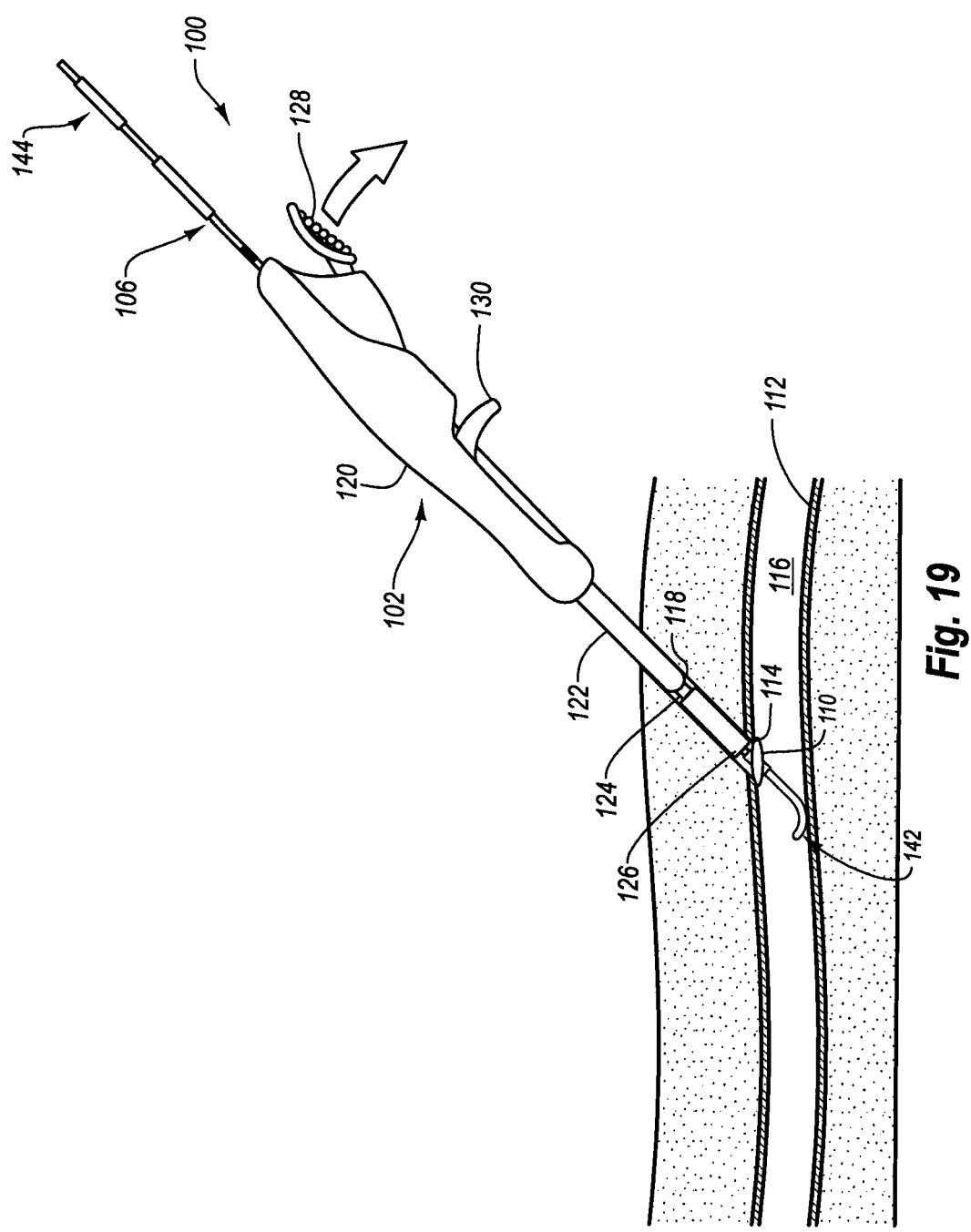
FIG. 19 is a side view of the tissue puncture treatment assembly of FIG. 18 with the sealing pad delivery device released from the locator wire.
Figure 20:
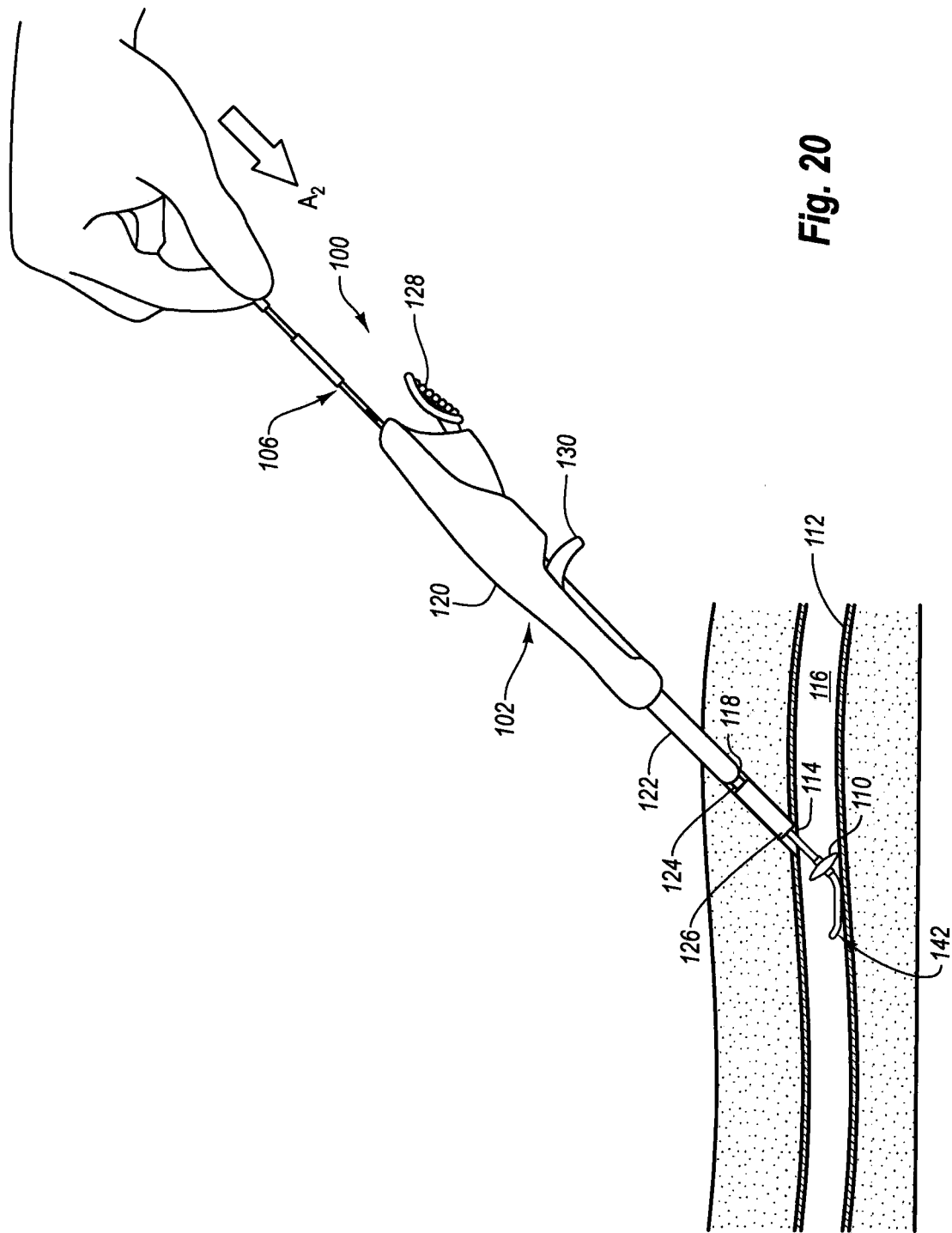
FIG. 20 is a side view of the tissue puncture treatment assembly of FIG. 19 with the locator wire advanced distally to separate the expanded column member from the vessel wall.

Referring now to FIG. 19, the wire locking member 128 is released so that the sealing pad delivery device 102 may be moved relative to the locator wire 106. The locator wire 106 is then advanced distally in the direction $A_2$ as shown in FIG. 20 until the column member 110 is moved out of contact with the inner wall of the vessel 112.

Figure 21:
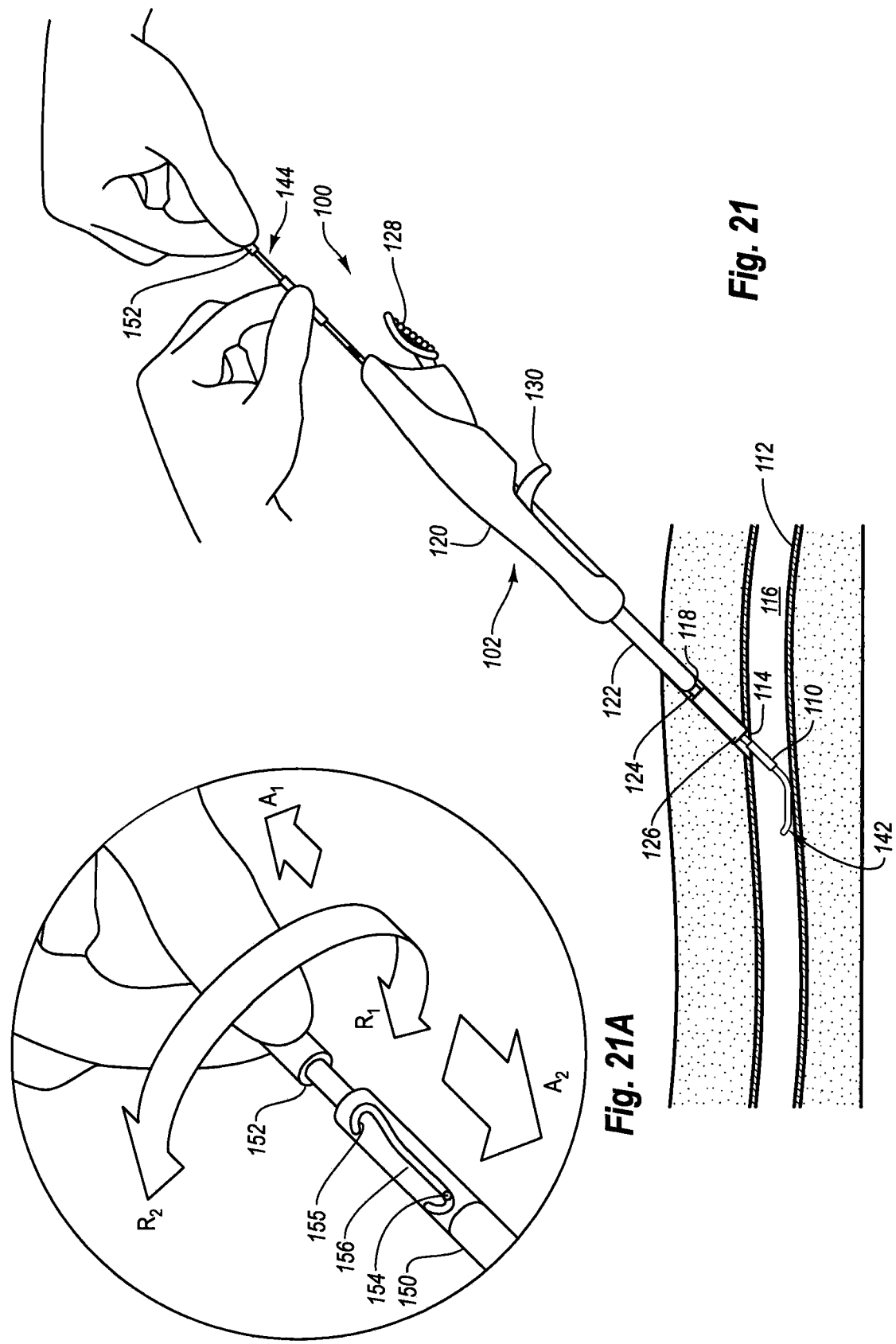

FIGS. 21 and 21A illustrate the column member 110 moved into the uncompressed, unexpanded state after being spaced distally away from the vessel puncture 114. The operator rotates the compression member 148 relative to the locator tube 140 in the direction $R_1$, to move the follower member 154 out of locking portion 155B, followed by applying a force to the locator tube 140 in the distal direction $A_2$ via the first grasp member 150 and applying an opposite force to the compression member 148 in the proximal direction $A_1$ via the second grasping member 152. After the follower member 154 reaches a proximal end of the track 156, the operator rotates the compression member 148 in the direction $R_2$ to move the follower member 154 into the locking portion 155A. The maximum width dimension of the column member 110 is reduced from a size $D_4$ to a size that is smaller than the maximum dimension of the vessel puncture 114 (e.g., dimension $D_3$).

Figure 22:
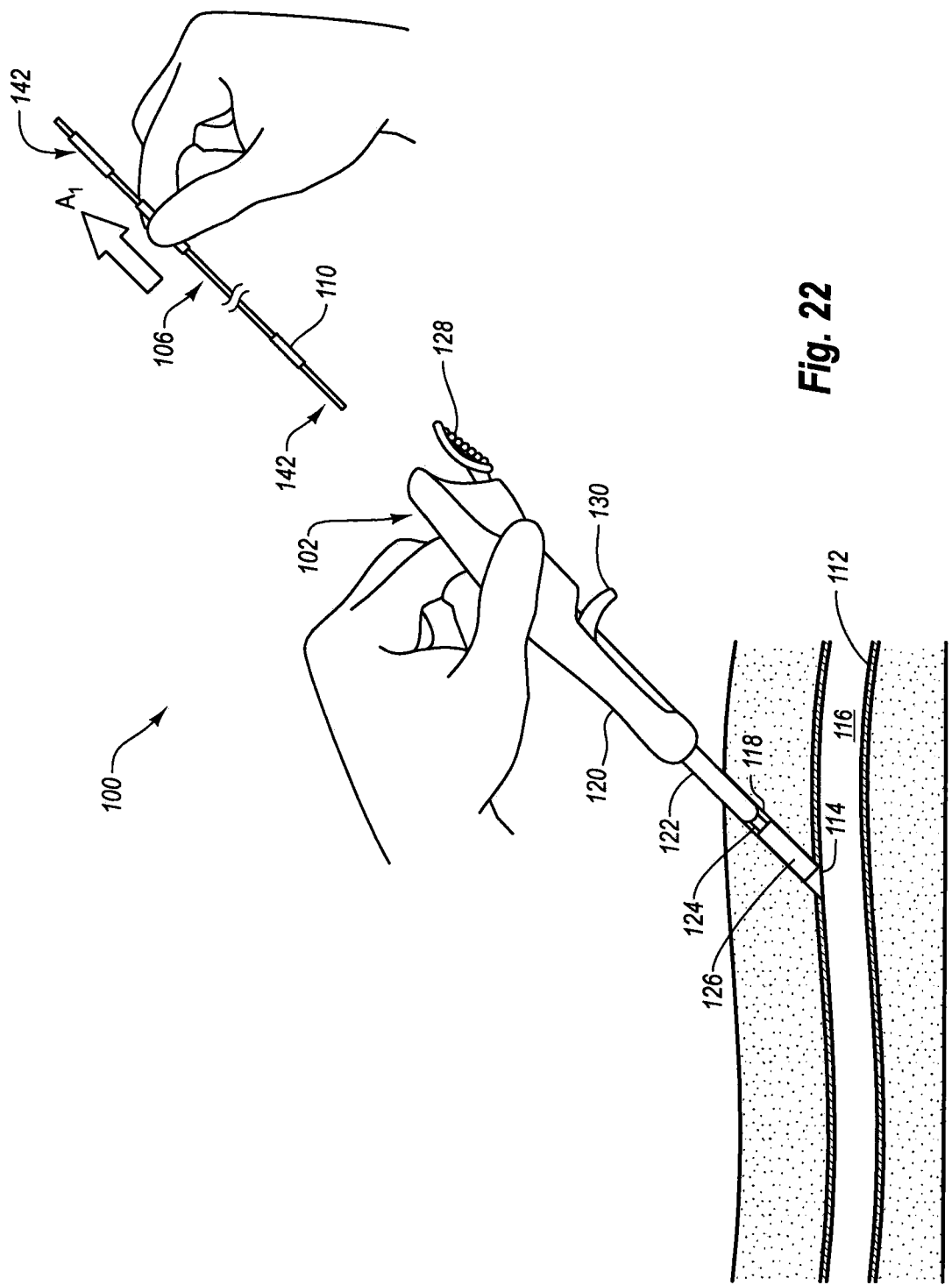
FIG. 22 is a side view of the tissue puncture treatment assembly of FIG. 21 with the locator wire being retracted through the sealing pad and removed from the sealing pad delivery device.

Referring now to FIG. 22, the locator wire 106 is advanced proximally in the direction $A_1$ out of the vessel 112, through the sealing pad 126, and out of the sealing pad delivery device 102 while holding the sealing pad delivery device 102 in a fixed position relative to the vessel 112.

Referring now to FIG. 23, the sealing delivery device 102 is retracted proximally in the direction $A_1$ while leaving behind the sealing pad 126 within the percutaneous incision 118. Typically the sealing pad 126 comprises an expandable material that expands to fill the percutaneous incision 118 at least at a location adjacent to the vessel puncture 114. In at least one example, the sealing pad 126 comprises a collagen material. The sealing pad 126 is typically configured to provide hemostasis in the vessel puncture 114 and percutaneous incision 118.

Many other constructions are possible for the various features of the tissue puncture treatment assembly 100 described above with reference to the attached figures. In particular, the aspects of the locator wire 106 including various arrangements for the column member 10, 110 described above may be changed or modified in accordance with the teachings provided herein.

Furthermore, alternative methods and treatment techniques using the compressible column structures disclosed herein may be used. In one alternative method, locating the vessel puncture using the column structure in the compressed state may occur concurrently with deploying the sealing pad within the percutaneous incision. In one example, the tissue puncture sealing device is assembled with the sealing pad arranged at a fixed distance from the column member and simultaneously exposed in the percutaneous incision adjacent to the tissue puncture while locating the vessel puncture with the expanded column member.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture locator device, comprising:
   a temporary anchor member configured for placement through a vascular puncture into a vessel, the temporary anchor member including a column member that defines a lumen, the column member having a reduced thickness portion, the reduced thickness portion having an outer surface that is continuous around a circumference of the reduced thickness portion at the lumen, the outer surface comprising a plurality of outer recesses along a length of the column member, the reduced thickness portion having an inner surface with an inner recess, the temporary anchor member being movable between an uncompressed position and a compressed position;
   wherein in the compressed position the outer surface at the circumference expands radially outward within the vessel to a maximum diameter that limits retraction of the temporary anchor member through the vascular puncture, wherein in the compressed position the plurality of outer recesses of the outer surface flatten into a single radially expanded outer surface at the maximum diameter, the single radially expanded outer surface being continuous around the circumference at the maximum diameter.

2. The tissue puncture locator device of claim 1, further comprising a compression member adapted for operation outside of a patient to move the temporary anchor member between the uncompressed and compressed positions.

3. The tissue puncture locator device of claim 1, wherein the column member comprises an elastic material.

4. The tissue puncture locator device of claim 1, wherein the column member comprises a polymer material.

5. The tissue puncture locator device of claim 1, wherein the uncompressed position permits passage of the temporary anchor member through the vascular puncture.

6. The tissue puncture locator device of claim 5, further comprising a sealing member configured for placement adjacent to the vascular puncture along an outer surface of the vessel, wherein the uncompressed position permits passage of the temporary anchor member through the sealing member after placement of the sealing member adjacent to the vascular puncture.

7. The tissue puncture locator device of claim 1, wherein the inner recess is a concave recess.

8. The tissue puncture locator device of claim 7, wherein the concave recess is annular.

9. The tissue puncture locator device of claim 1, wherein at least one of the outer recesses is annular.

10. The tissue puncture locator device of claim 1, wherein the reduced thickness portion is molded into the column member.

11. A tissue puncture closure device adapted for partial insertion into and sealing of a tissue puncture in an internal tissue wall accessible through a percutaneous incision, the device comprising:
- a temporary anchor configured to be disposed on a distal side of the internal tissue wall, the temporary anchor including a column structure and a lumen extending through the column structure, the column structure having a reduced wall thickness portion around the lumen at a location along a length of the column structure, the reduced wall thickness portion having an outer surface that is continuous around a circumference of the reduced wall thickness portion, the outer surface having a plurality of adjacent outer surface recesses along the length of the column structure, the column structure having an internal surface and an internal surface recess formed in the internal surface, the temporary anchor having a compressed state wherein the outer surface at the circumference expands radially outward in a manner flattening and substantially eliminating the plurality of adjacent outer surface recesses into a single radially expanded outer surface configured to limit movement through the vascular puncture, the single radially expanded outer surface having a continuous maximum outer circumference around the lumen, the temporary anchor having an uncompressed state wherein the temporary anchor is configured to move through the tissue puncture.

12. The tissue puncture closure device of claim 11, wherein the lumen extends along at least a portion of the length of the column structure.

13. The tissue puncture closure device of claim 11, further comprising a compression member arranged and configured to move the temporary anchor between the compressed and uncompressed states.

14. The tissue puncture closure device of claim 11, wherein the temporary anchor is configured to occlude blood flow through the tissue puncture when in the compressed state.

15. A method of locating a tissue puncture in an internal tissue through a percutaneous incision using a temporary anchor, the method comprising:
- inserting the temporary anchor into the percutaneous incision, the temporary anchor comprising a hollow cylindrical member, the hollow cylindrical member comprising an outer surface, an inner surface, a lumen, and a length, the length comprising a reduced thickness portion and a plurality of out recesses positioned on the outer surface along the length, the outer surface having a continuous circumference at the reduced thickness portion, the circumference extending around the lumen, the inner surface having an inner recess;
- applying an axially directed force to the temporary anchor that radially expands the outer surface at the circumference, the plurality of the outer recesses flattening into a radially expanded outer surface and being substantially eliminated at the circumference when the outer surface is expanded;
- retracting the temporary anchor proximally until the radially expanded outer surface of the hollow cylindrical member contacts the internal tissur wall adjacent the tissue punture.

16. The method of claim 15, wherein applying the axially directed force includes applying a compression force to the temporary anchor in a distal direction.

17. The method of claim 15, wherein the inner recess is molded into the hollow cylindrical member.

18. A tissue puncture locator device, comprising:
- a temporary anchor member configured for placement through a vascular puncture into a vessel, the temporary anchor member including a column member that defines a lumen, the column member having a reduced thickness portion, the reduced thickness portion having an outer surface that is continuous around a circumference of the reduced thickness portion, the outer surface comprising a plurality of outer recesses along a length of the column member, the reduced thickness portion having an inner surface with an inner recess, the temporary anchor member being movable between an uncompressed position and a compressed position, wherein in the compressed position a portion of the column member expands radially outward within the vessel to a size that limits retraction of the temporary anchor member through the vascular puncture, wherein in the compressed position the plurality of outer recesses flatten into a single radially expanded portion; wherein at least one of the outer recesses is annular.

* * * * *